US00PP35105P2

(12) United States Plant Patent
Bowen, III

(10) Patent No.: US PP35,105 P2
(45) Date of Patent: Apr. 11, 2023

(54) ***BERGENIA* PLANT NAMED 'RIPPLE EFFECT'**

(50) Latin Name: ***Bergenia* hybrid**
Varietal Denomination: Ripple Effect

(71) Applicant: Edward H Bowen, III, Little Compton, RI (US)

(72) Inventor: Edward H Bowen, III, Little Compton, RI (US)

( * ) Notice: Subject to any disclaimer, the term of this patent is extended or adjusted under 35 U.S.C. 154(b) by 0 days.

(21) Appl. No.: 17/803,698

(22) Filed: Oct. 13, 2022

(51) Int. Cl.
*A01H 5/02* (2018.01)
*A01H 6/80* (2018.01)

(52) U.S. Cl.
USPC ..... Plt./409

(58) Field of Classification Search
USPC ..... Plt./409
CPC ..... A01H 5/02; A01H 5/00; A01H 6/80
See application file for complete search history.

(56) References Cited

U.S. PATENT DOCUMENTS

PP32,132 P2 * 8/2020 Hansen ..... A01H 6/80
Plt./409

* cited by examiner

*Primary Examiner* — June Hwu

(57) ABSTRACT

A new and distinct Fringed *Bergenia* hybrid, *Bergenia* plant named 'Ripple Effect' with medium-sized, mounded habit, with large, densely-arranged, deep-green, glossy, obovate, deciduous leaves, and white campanulate flowers developing a pinkish blush with maturity, on heavily-branched, large panicles over at least a three-week period beginning in early spring. The flowers hold up well in the garden as a landscape plant or as cut flowers. The new plant has a vigorous growth rate and is naturally resistant to deer and rabbit foraging.

1 Drawing Sheet

Botanical designation: *Bergenia* hybrid.
Cultivar denomination: 'Ripple Effect'.

STATEMENT REGARDING PRIOR DISCLOSURES UNDER 37 CFR 1.77(b)(6)

The original information of the claimed plant was made by Walters Gardens, Inc. on Feb. 1, 2022, when the claimed plant was displayed as a photograph with a non-enabling brief description in a website maintained by Walters Gardens, Inc., This was followed by the listing with a brief description and photograph in the "Walters Gardens 2022-2023 Catalog." Walters Gardens, Inc. obtained the plant and all information relating thereto, from the inventor. Plants of *Bergenia* 'Ripple Effect' have not been sold, in this country or anywhere in the world as of the filing date of this application, nor has any enabling disclosure of the new plant been made, more than one year prior to the filing date of this application, and such disclosure within one year was either derived directly or indirectly from the inventor.

BACKGROUND OF THE PLANT

The present invention relates to the new and distinct Heartleaf *Bergenia* herein also referred to as *Bergenia* 'Ripple Effect', by the cultivar name, 'Ripple Effect', or as the new plant. The new plant was hybridized by the inventor in March of 2011, between a plant of *Bergenia ciliata* 'Susan Ryley' (not patented) as the female and a proprietary unnamed selection of *Bergenia pacumbis*, in a nursery in Little Compton, R.I. The single seedling represented by 'Ripple Effect' was selected from a group of seedlings by the inventor, isolated initially in 2012, and compared in subsequent years to other *Bergenia* and subsequently found to be different from all cultivars known to the inventor.

Asexual propagation at the same nursery initially by division in 2013, and later by shoot tip sterile tissue culture has shown 'Ripple Effect' to be stable and reproduce true to type in successive generations.

SUMMARY OF THE PLANT

*Bergenia* 'Ripple Effect' has not been observed in all possible environmental conditions. The phenotype may vary slightly with changes in environments such as light intensity, fertility, water availability, etc. without, however any variation in genotype.

*Bergenia* 'Ripple Effect' is distinct from all cultivars known to the inventor in the following traits:

1. Medium-sized, mounded habit;
2. Very large, densely-arranged, medium-green, glossy, broadly-obovate, deciduous foliage;
3. Leaves have a crenate sinuate margin;
4. Large heavily-branched panicle with white bell-shaped flowers over a long period in the early spring;
5. Flowers developing pinkish blush with age;
6. Medium growth rate;
7. Naturally resistant to deer and rabbits.

The female parent has more pinkish flowers. The male parent has less undulate and ciliolate margins, and the surface is more bullate. The most similar plants known to the inventor are: 'Sakura' (not patented), 'Flirt' U.S. Plant Pat. No. 26,355, 'Miss Piggy' U.S. Plant Pat. No. 32,132, and 'Pink Dragonfly' (not patented). 'Sakura' has larger pink flowers that are held tighter together on smaller plants and smaller foliage. 'Miss Piggy' has foliage that is not quite as large, and the flowers open more light pink. 'Flirt' has smaller inflorescences and deeper pink flowers over a shorter period of time on much smaller plants. 'Pink Dragonfly' has slightly deeper pink flowers on smaller inflorescences, much smaller foliage, and smaller habit. None of the above cultivars have sinuate, ciliolate foliage that is as large as 'Ripple Effect'.

BRIEF DESCRIPTION OF THE DRAWING

The color drawing illustrates the overall characteristics of *Bergenia* 'Ripple Effect' as a four-year-old plant. The colors are as true as reasonably possible given the technology available. The color values may vary slightly depending on light intensity and quality.

The drawing identified as FIG. 1 shows the new plant in a landscape environment with flowers and young and more mature foliage.

DETAILED BOTANICAL DESCRIPTION

The following description is based on two-year-old plants growing in a two-gallon container in a partially-shaded greenhouse and in a shaded trial garden in Little Compton, R.I., USA. Except for ordinary dictionary color usage, color references are according to The Royal Horticultural Society Colour Chart, 1966 edition. The new plant has not been observed in all possible growing conditions and may vary in phenotypic characteristics based on water availability, light conditions, fertilizer, temperatures, etc. without varying in genotypic characteristics.

Parentage: Female or seed parent 'Susan Ryley'; male or pollen parent is a proprietary selection of *Bergenia pacumbis;*

Asexual propagation: Division of tissue culture plants, about 21 days to initiate roots; time to flowering from 25-mm plugs in a one-gallon container about 3 months; moderate growth rate;

Plant habit: Rhizomatous, spreading, mounded, herbaceous, winter-hardy, perennial mound; with heavily branched flower stems; with about 10 stems per plant; shoots to about 5 cm long and about 1.2 cm diameter;

Plant size: Foliage up to about 70 cm wide and about 30 cm tall; flowering to about 25 cm tall and about 50 cm wide;

Growth rate: Vigorous; taking about 2 weeks to root in tissue culture; flowering in a 3.8-liter container in about 6 to 8 weeks from a 65 mm plug;

Roots: Fibrous; highly branched to about 18 cm long; to about 3 mm diameter; color variable with soil matrix, about RHS 165B;

Leaves: Alternate; simple; coriaceous; broadly obovate; adaxial and abaxial surface lustrous; rounded apex; attenuate base; margin crenate, undulate, ciliolate; up to 35 cm long and 32 cm wide, average about 30 cm long and about 27 cm wide;

Leaf color: Young expanding leaves adaxial about RHS 147B and abaxial about RHS 82A with emerging adaxial and abaxial margin about RHS 181D; mature leaves adaxial about RHS 137B, abaxial about RHS 145B; winter color not available, deciduous;

Veins: Pinnate; impressed adaxial, penniveined abaxial;

Vein color: Adaxial about RHS 143C, abaxial about RHS 145D;

Petiole: Sheathing clasping base, ciliate margin; glabrous adaxial and abaxial; to about 16 cm long and 1.5 cm wide;

Petiole color: Emerging adaxial about 178C, abaxial about 48B; mature adaxial about 138A, abaxial about 145A;

Inflorescence: Scapose cyme; about 6 per plant; about 25 cm long and 9 mm diameter at base; cylindrical;

Peduncle: Cylindrical; lustrous;

Peduncle color: About RHS 151D proximally, middle and distally about RHS 31C; near end of the flowering season about RHS 152B;

Flower: Single; perfect; rotate; campanulate; on terminal branches; about 20 to 30 mm across, about 15 to 20 mm tall, corolla to 19 mm wide and 20 mm tall; attitude outright to slightly drooping;

Flower fragrance: Light lilac-like;

Calyx: Campanulate; to about 15 mm wide and 8 mm tall;

Sepals: Typically five; ovate; obtuse apex; truncate base, fused in basal 7 mm; margin entire; glabrous and lustrous adaxial; abaxial micro-glandular, slightly lustrous; about 13 mm long and about 7 mm wide at fusion;

Sepal color: Adaxial about RHS 145A with thin picotee margin about RHS 48A, abaxial about RHS 178B; other sepals adaxial nearest RHS 145A with thin picotee margin about RHS 48A;

Flowering period: Beginning early spring, for at least 3 weeks; producing up to 75 flowers per branched stem and 20 flowers per branch;

Flower longevity: 7 to 10 days;

Flower buds one day prior to opening: Ovoid; acute apex; about 14 mm long and 1.2 mm diameter;

Flower bud color one day prior to opening: Exposed petals about RHS 155C, sepals about RHS 66C;

Pedicel: Cylindrical; glaucous; lustrous; about 11 mm to 15 mm long and 2 mm diameter;

Pedicel color: About RHS 152B;

Petals: Typically, five in a single whorl, rarely six; obovate; obtuse apex; attenuate base; margin entire; glabrous adaxial abaxial; imbricate near longitudinal middle; about 15 mm long and 10 mm wide near middle;

Petal color: Variable; when initially open basal portion adaxial and abaxial about RHS 74D, distal adaxial about RHS 155C and abaxial about RHS 155B; when flower is mature basal portion adaxial and abaxial about RHS 74C, distal adaxial portion about RHS 74D with a picotee margin about RHS 155C, distal abaxial portion about RHS 74D with a picotee margin about RHS 155D;

Androecium: Typically ten; about 9 mm long;

*Filament*.—About 8 mm long and 0.7 mm diameter; color about RHS 55B.

*Anther*.—Ellipsoidal; basifixed; longitudinal; about 1 mm long and 1 mm across; color about RHS 201B.

*Pollen*.—Abundant; color about RHS 155C.

Gynoecium: Double; about 11 mm long;

*Ovary*.—Partly inferior.

*Style*.—Cylindrical; about 9 mm long and 3 mm diameter above ovary; color at opening about RHS 49B, color at maturity about RHS 49D.

*Stigma*.—Loosely lobed; about 1 mm tall and 2 mm wide; color about RHS 197A.

Seed: Has not been observed;

*Bergenia* 'Ripple Effect' is tolerant of winter temperatures from USDA hardiness at least from zones 5 to 9. The new plant grows best with good drainage and adequate moisture. It is not known to be tolerant of diseases and pest that are common to other Fringed *Bergenia* hybrid cultivars.

It is claimed:

1. A new and distinct cultivar of *Bergenia* plant named 'Ripple Effect' as described and illustrated.

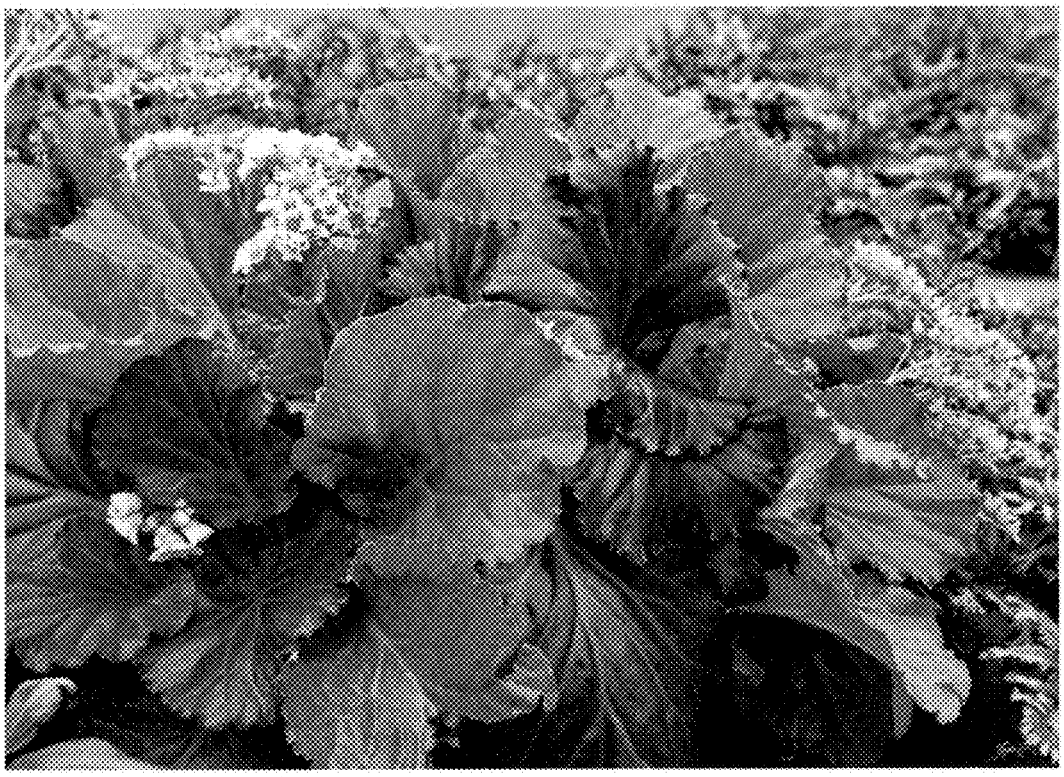

* * * * *